United States Patent

Yeh et al.

[11] Patent Number: 6,153,497
[45] Date of Patent: Nov. 28, 2000

[54] METHOD FOR DETERMINING A CAUSE FOR DEFECTS IN A FILM DEPOSITED ON A WAFER

[75] Inventors: Renn-Shyan Yeh, Taichun; Der-Fang Huang, Hsin-Chu; Chao-Hsin Chang, Tao-Yuan; Chih-Chien Hung, Hsin-Chu, all of Taiwan

[73] Assignee: Taiwan Semiconductor Manufacturing Co., Ltd, Hsin Chu, Taiwan

[21] Appl. No.: 09/281,335

[22] Filed: Mar. 30, 1999

[51] Int. Cl.[7] .................................................. H01L 21/425
[52] U.S. Cl. .......................... 438/515; 438/458; 438/800; 438/510
[58] Field of Search ..................... 438/515, 800, 438/510, 455, 766, 798, 148, 458, 459, 526, 974, 527; 430/5, 322, 582

[56] References Cited

U.S. PATENT DOCUMENTS

| | | | |
|---|---|---|---|
| 5,472,143 | 12/1995 | Bartels et al. | 239/462 |
| 5,538,816 | 7/1996 | Hasimoto et al. | 430/5 |
| 6,013,563 | 1/2000 | Henley et al. | 438/458 |
| 6,013,567 | 1/2000 | Henley et al. | 438/515 |

FOREIGN PATENT DOCUMENTS 2253498  10/1972  Germany ................... 17/22

*Primary Examiner*—Charles Bowers
*Assistant Examiner*—Laura Schillinger
*Attorney, Agent, or Firm*—Tung & Associates

[57] ABSTRACT

A method for determining a cause for defect formation in an insulating material layer deposited on an electrically conductive layer on a wafer surface is disclosed. In the method, on top of a semi-conducting wafer which has a first insulating material layer deposited, a second insulating material layer is deposited to replace an electrically conductive layer. A third insulating material layer is then deposited on top of the second insulating layer and a water jet which has a high pressure is scanned across a top surface of the third insulating layer with the wafer held in a stationary position. Surface defects are then counted in the predetermined path on the top surface of the third insulating layer for determining the cause for defect formation. When no defects are found, the formation is attributed to electrostatic discharges occurring in the metal conductive layer.

18 Claims, 2 Drawing Sheets

Via-cracks Were Occured Along The Route of Jet.

METHOD FOR DETERMINING A CAUSE FOR DEFECTS IN A FILM DEPOSITED ON A WAFER

FIELD OF THE INVENTION

The present invention generally relates to a method for determining causes for defects in a film deposited on a wafer and more particularly, relates to a method for determining causes for defects in an insulating layer deposited on a silicon wafer due to mechanical stresses or electrostatic discharge.

BACKGROUND OF THE INVENTION

In the fabrication process for semiconductor devices, numerous fabrication steps, as many as several hundred, must be carried out on a silicon wafer in order to complete the circuits needed for the devices. Since the processing of silicon wafers requires extreme cleanliness in the processing environment and that no contaminating particles or films are allowed, the surface of the wafer must be cleaned after each processing step. For instance, it is cleaned after the deposition of a coating layer such as oxide or after the formation of a circuit in a processing step such as etching. A frequently used method for cleaning the wafer surface is wet scrubbing.

In a wet scrubbing method, a wafer is rotated at a high speed, i.e., at least 200 RPM and preferably 1,000 RPM with a jet of high pressure deionized water sprayed on top. The water jet is normally sprayed at a pressure of about 2,000~3,000 psi. The water movement on the top surface of the wafer displaces any contaminating particles that are lodged on the wafer surface. One limitation of the water jet scrubbing method is that the process only moves particles from side to side in openings, such as oxide windows, without actually removing the particle. Furthermore, as image size decreases, it becomes more difficult for water to reach the particles in openings because of increased surface tension.

It has also been noted that in a water jet scrubbing process conducted on a silicon wafer that is coated with an insulating material, i.e., an oxide layer as an inter-metal dielectric layer, some regions of the film is damaged at the wafer center by the cumulated stress from the water jet when the aperture size of the jet nozzle is too large or is distorted. The damaged film can be identified by a KLA scan, even though a large number of wafers must be tested since the probability of such damage is only about 10~30%. This is shown in FIGS. 1 and 2.

FIG. 1 shows an illustration of a silicon wafer surface that is scanned in a conventional water jet scrubbing method. Wafer 10 is normally positioned on a wafer platform (not shown) situated in a scrubbing apparatus and rotated at a predetermined rotational speed. A suitable rotational speed may be between 200 RPM and 2,000 RPM. The centrifugal force acting on the water flow on the wafer surface removes contaminating particles or films. The jet of deionized water which has a water pressure of approximately 50 kg/cm², is scanned on top of the wafer surface along trace 12 which normally runs through wafer center 14. The wafer surface is scanned by the water jet at least once, and preferably several times.

A KLA scan on a wafer surface coated with an oxide film layer and scanned by a high pressure water jet is shown in FIG. 2. The black dots shown on the surface of the wafer indicate stress defects that have formed under the water jet pressure.

It has been noted that the stress defects only occur on certain types of surface coating layers and only for certain thicknesses of layers coated on a wafer surface. In the conventional water jet cleaning method, as shown in FIG. 1, it is difficult to identify which type of films will be damaged since the defects or damages are occurring only randomly at the wafer center. Furthermore, it is difficult to monitor whether the aperture in the jet nozzle is distorted or deformed.

A further complication in determining a cause for a surface defect in a coated film is that the defect may be caused by electrostatic discharge (ESD) damage which may have the same appearance. Since surface defects in the form of cracks were discovered in a layer of insulating material that was deposited on a metal layer and furthermore, SEM images showed that the metal layer has exploded, the cause of defect formation may very well be due to electrostatic discharge instead of mechanical stresses in the insulating layer. To verify the causes for surface defects, the electrostatic fields in two separate scrubbers, i.e., a first scrubber which does not present the surface defect problem and a second scrubber which has exhibited a high surface defect rate, were measured in a wet scrubber with the scrubber jet turned on. A higher electrostatic field was measured in the second scrubber chamber. It presents a strong correlation between the electrostatic discharge and the surface defects. The electrostatic field was reduced after an electrically conductive chuck was used in the second scrubber which did not stop the surface defect formation. However, the possibility that surface defects are caused by electrostatic discharges still cannot be ruled out since electrostatic discharges may take place instantaneously when a water jet touches the wafer. In such instance, an electrical charge flows to the conductive chuck so rapidly that the measuring device can not measure a change in the electrostatic discharge. As a result, the true cause for the surface defects, i.e., whether by mechanical stresses imposed in a scrubber clean process or by an electrostatic discharge from the metal layer underneath cannot be ascertained.

It is therefore an object of the present invention to provide a method for determining a cause for defects in a film layer deposited on a wafer surface that does not have the drawbacks or shortcomings of the existing measurement techniques.

It is another object of the present invention to provide a method for determining a cause for defects in a film layer deposited on a wafer surface as due to mechanical stresses or due to electrostatic discharge.

It is a further object of the present invention to provide a method for determining a cause for defects in a film layer deposited on a wafer surface by first eliminating a possible cause of electrostatic discharge.

It is another further object of the present invention to provide a method for determining a cause for defects in a film layer deposited on a wafer surface by substituting a metal layer deposited under an insulating material layer with a second insulating material layer.

It is still another object of the present invention to provide a method for determining a cause for defects in an insulating material layer deposited on a wafer surface by substituting an aluminum layer with a silicon nitride layer underneath the layer of insulating material.

It is yet another object of the present invention to provide a method for determining a cause for defects in a film layer deposited on a wafer by first substituting a metal layer underneath the film layer with a second insulating layer and then scanning a water jet across a top surface of the film layer to detect any defects formed by the water jet pressure.

It is still another further object of the present invention to provide a method for testing a wafer that has a metal conductive layer and an inter-metal dielectric layer sequentially deposited on top by substituting the metal conductive layer with a second insulating material layer and then injecting a water jet of at least 50 kg/cm$^2$ pressure on top of the inter-metal dielectric layer to detect defects formed by the water jet pressure.

It is yet another further object of the present invention to provide a method for testing a wafer which has an aluminum layer and an oxide layer sequentially deposited on top by first substituting the aluminum layer with a silicon nitride layer and then injecting a water jet of at least 50 kg/cm$^2$ pressure on top of the oxide layer to detect any formation of stress cracks caused by the high pressure water jet.

SUMMARY OF THE INVENTION

In accordance with the present invention, a method for determining a cause for defect formation in an insulating film material deposited on an electrically conductive layer on a wafer is disclosed.

In a preferred embodiment, a method for determining a cause for defect formation in an insulating film layer deposited on an electrically conductive metal layer on a wafer can be carried out by the operating steps of providing a semi-conducting wafer which has a first insulating layer deposited on top, depositing a second insulating layer on top of the first insulating layer, the second insulating layer being deposited in place of an electrically conductive layer, depositing a third insulating layer on top of the second insulating layer, scanning a water jet which has a pressure of at least 50 kg/cm$^2$ across a top surface of the third insulating layer in a predetermined path while the wafer is held in a stationary position, and counting defects formed in the predetermined path on the top surface of the third insulating layer.

In the method for determining a cause for defect formation, the first and third insulating layers are formed of a material different than that used in forming the second insulating layer. The method may further include the step of determining whether any defects formed are caused by the water jet. The method may further include the step of, when no defects are found after the water jet scanning step, determining that defects previously observed in the third insulating layer when deposited on an electrically conductive layer are caused by electrostatic discharge.

In the method, the first and third insulating layers may be formed of silicon oxide, while the second insulating layer may be formed of silicon nitride. The electrically conductive layer may be a metal layer. The third insulating layer may be an inter-metal dielectric layer. The first and third insulating layers may be inter-metal dielectric layers. The method may further include the step of scanning the water jet with a pressure of preferably at least 50 kg/cm$^2$. The method may further include the step of scanning the water jet across a top surface of the third insulating layer in a path through a center of the semi-conducting wafer.

The present invention is further directed to a method for testing a wafer which has a metal conductive layer and an inter-metal dielectric (IMD) layer deposited on top including the operating steps of providing a silicon wafer which has a first IMD layer deposited on top, depositing a second insulating layer in place of a metal conductive layer overlying the first IMD layer, depositing a third IMD layer overlying the second insulating layer, injecting a water jet of at least 60 kg/cm$^2$ pressure along a predetermined path on the third IMD layer, observing any defects formed in the third IMD layer along the predetermined path, determining a cause for defects by water jet pressure when defects are found, and determining a cause for similar defects previously found as electrostatic discharge when no defect is found.

In the method for testing a wafer which has a metal conductive layer and an IMD layer sequentially deposited on top, the first and third IMD layers may be formed of silicon oxide. The second insulating layer deposited may be silicon nitride. The metal conductive layer may be formed of aluminum or copper. The first and third IMD layers may be formed of a material different than that used in forming the second insulating layer. The method may further include the step of scanning the water jet with a pressure of preferably at least 50 kg/cm$^2$. The method may still further include the step of scanning the water jet across a top surface of the third IMD layer in a path through a center of the semi-conducting layer.

BRIEF DESCRIPTION OF THE DRAWINGS

These and other objects, features and advantages of the present invention will become apparent from the following detailed description and the appended drawings in which.

DETAILED DESCRIPTION OF THE PREFERRED EMBODIMENT

The present invention discloses a method for determining a cause for defect formation in an insulating material layer deposited on an electrically conductive layer on a wafer. In the method, on top of a semi-conducting wafer which has a first insulating layer deposited, a second insulating material layer is deposited in place of an electrically conductive layer that was originally deposited. A third insulating material layer is then deposited on top of the second insulating material layer and a water jet which has a pressure of at least 50 kg/cm$^2$ is scanned across a top surface of the third insulating material layer in a predetermined path with the wafer held in a stationary position. Surface defects formed are then counted in the predetermined path on the top surface of the third insulating material layer. When no defects are formed, the cause for defect formation observed previously in an insulating material layer deposited on top of an electrically conductive layer can be attributed to electrostatic discharges that occurred in the conductive layer. The method may further be conducted by scanning a water jet across the top surface of the third insulating material layer at a water pressure of at least 50 kg/cm$^2$.

The present invention further discloses a method for testing a wafer which has a metal conductive layer and an inter-metal dielectric (IMD) layer sequentially deposited on top by first providing a silicon wafer which has a first IMD layer of oxide deposited on top, then depositing a second insulating material layer of nitride instead of a metal conductive layer overlying the first IMD layer, then depositing a third IMD layer of oxide overlying the second insulating material layer. A water jet which has a pressure of at least 60 kg/cm² is then scanned along a predetermined path on the third IMD layer and any defects formed on the surface is observed and counted. When defects are observed, it is an indication that the surface defects are formed by mechanical stresses caused by the water jet pressure. When no defects are found, it can be assumed that similar defects previously observed in the top IMD layer may be caused by electrostatic discharges in the metal conductive layer.

Figure 1:
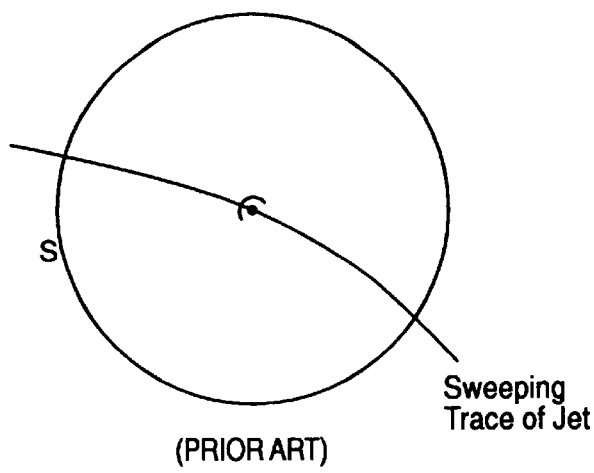
FIG. 1 is an illustration of a conventional method for cleaning a wafer positioned in a wet scrubber by a water jet traversing across a top surface and through a center of the wafer.
Figure 2:
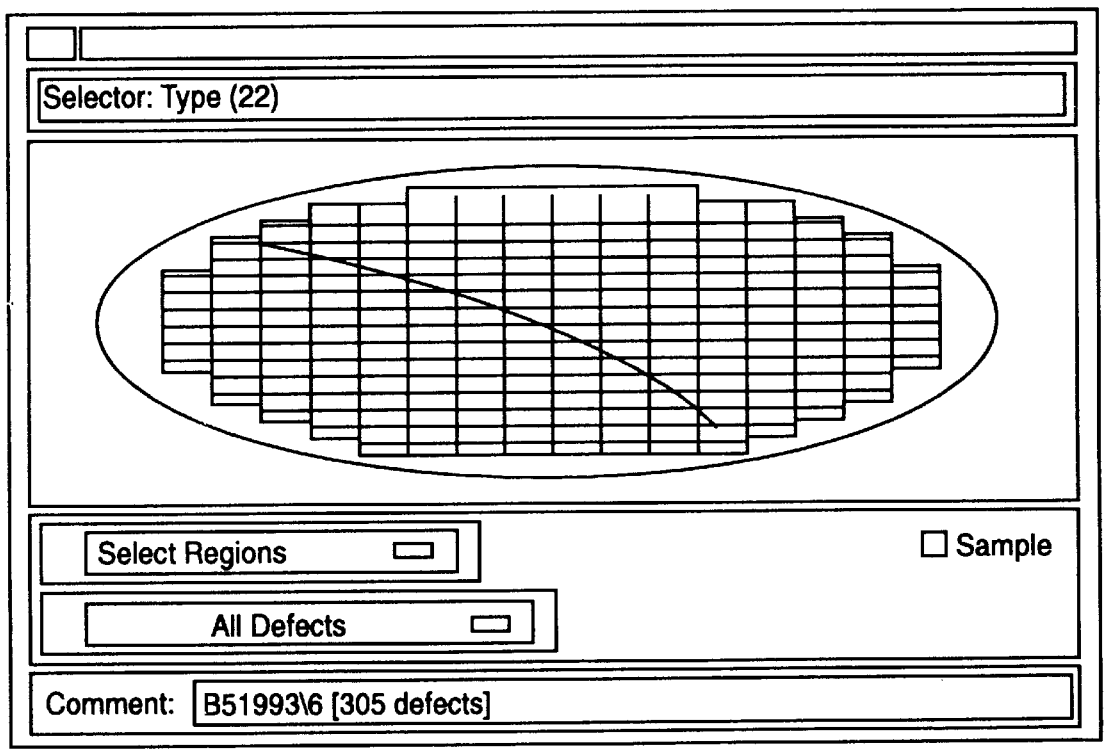
FIG. 2 is an illustration of a KLA scan obtained across a wafer surface that is scrubber cleaned by the conventional method of FIG. 1.
Figure 3:
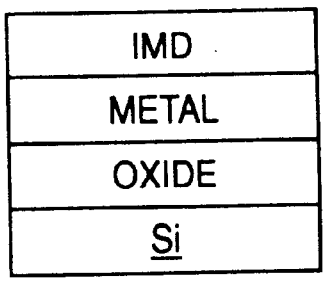
FIG. 3 is an enlarged, cross-sectional view of a conventional wafer structure having a metal conductive layer deposited between two insulating material layers.

The present invention novel method therefore utilizes an insulating material layer to replace an underlying metal layer to verify the role of electrostatic discharges or mechanical stresses caused by the water jet. Referring now to FIG. 3, wherein an enlarged, cross-sectional view of a conventional wafer structure 20 is shown. In the wafer structure 20, a silicon wafer 22 is first provided. On top of the silicon wafer 22, an insulating material layer 24 such as oxide is deposited overlying the silicon surface. An electrically conductive layer 26, such as a layer of aluminum is then deposited and patterned for forming interconnections for vias and conductors. On top of the metal layer 26, a second insulating material layer 28, i.e., an inter-metal dielectric (IMD)layer of PE oxide is then deposited to insulate the metal layer 26. On top of the IMD layer 28, further metal layers (not shown) and IMD layers (not shown) may be deposited to complete a multi-layer device structure. When the wafer structure 20 is cleaned in a wet scrubber, surface defects formed on the top surface 32 of the IMD layer 28 are frequently observed. Such defect formation cannot be diagnosed as being caused by mechanical stresses of the scrubber water pressure or being caused by electrostatic discharges occurred in the underlying metal layer 26.

Figure 4:
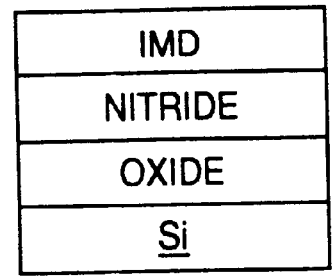
FIG. 4 is an enlarged, cross-sectional view of a wafer structure used in the present invention method in which a metal conductive layer is replaced by an insulating material layer such as nitride.

In the present invention method, as shown in FIG. 4, a wafer structure 40 which is built on a silicon wafer 42 is first presented. On top of the silicon wafer 42, an insulating material layer 44 such as an oxide layer is deposited. A second insulating material layer 46, such as a PE nitride material is then deposited overlying the first insulating layer 44. The layer 46 replaces the metal conductive layer 26 that was used in the conventional wafer structure 20 (FIG. 3). By utilizing the second insulating material layer 46, the cause of defects attributed by electrostatic discharges can be eliminated. A third insulating material layer 48, i.e., an IMD layer of PE oxide is then deposited on top of the second insulating layer 46. The IMD layer 48 has a top surface 52 that is normally cleaned in a wet scrubber by deionized water.

The present invention wafer structure 40 is then placed in a wet scrubber (not shown) and a high pressure deionized water jet is scanned across a top surface 52 of the wafer structure 40 in a predetermined path. The predetermined path may, or may not, go through the center of the wafer. A suitable water pressure used is at least 60 kg/cm², and preferably at least 70 kg/cm². The high water pressure may be achieved by using a water jet nozzle that has a large aperture, i.e., such as an aperture greater than 0.1 mm, and preferably greater than 0.15 mm. By using the present invention novel method, it is only necessary to perform the test on a single wafer and to scan the water jet on the wafer surface only once.

After the wafer structure 40 is scanned by the water jet, the surface 52 is examined under optical microscope or electron microscope for the observation of surface defects. When surface defects are formed along the predetermined path of the water jet scrubbing operation, the cause for the defect formation is confirmed as mechanical stress imposed by the water pressure.

When the surface 52 of the wafer structure 40 does not show the formation of defects in the predetermined scrubbing path, the cause for previously observed defect formation can be narrowed down to electrostatic discharges occurring in the metal conductive layer in the conventional structure, i.e., in the wafer structure 20 shown in FIG. 3. The present invention novel method therefore provides a reliable means for determining whether surface defects found on an insulating material layer, i.e., an IMD layer, on top of a wafer surface is caused by mechanical stresses of scrubbing water jet or by electrostatic discharges occurring in an underlying metal conductive layer. The present invention novel method can be advantageously carried out on a single wafer to determine causes for surface defects. The method can be executed by a single sweep of a high pressure water jet on the top surface of a wafer.

The present invention novel method for determining a cause for defect formation in an insulating material layer on top of a wafer surface has been amply demonstrated in the above descriptions and in the appended drawing of FIG. 4.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

What is claimed is:

1. A method for determining a cause for defect formation in an insulating material layer deposited on an electrically conductive layer on a wafer surface comprising the steps of:

providing a semi-conducting wafer having a first insulating layer deposited on top, depositing a second insulating layer on top of said first insulating layer, said second insulating layer being deposited in place of an electrically conductive layer, depositing a third insulating layer on top of said second insulating layer, scanning a water jet having a pressure of at least 50 kg/cm² across a top surface of said third insulating layer in a predetermined path with said wafer held in a stationary position, and counting defects formed in said predetermined path on said top surface of the third insulating layer.

2. A method for determining a cause for defect formation in an insulating material layer deposited on an electrically conductive layer on a wafer surface according to claim 1, wherein said first and third insulating layers are formed of a material different from that used in forming said second insulating layer.

3. A method for determining a cause for defect formation in an insulating material layer deposited on an electrically conductive layer on a wafer surface according to claim 1 further comprising the step of determining whether any defects formed are caused by said water jet.

4. A method for determining a cause for defect formation in an insulating material layer deposited on an electrically conductive layer on a wafer surface according to claim 1 further comprising the step of when no defects are found after said water jet scanning step, determining that defects previously observed in said third insulating layer when deposited on an electrically conductive layer as caused by electrostatic discharges.

5. A method for determining a cause for defect formation in an insulating material layer deposited on an electrically conductive layer on a wafer surface according to claim 1, wherein said first and third insulating layers are formed of silicon oxide.

6. A method for determining a cause for defect formation in an insulating material layer deposited on an electrically conductive layer on a wafer surface according to claim 1, wherein said second insulating layer is formed of silicon nitride.

7. A method for determining a cause for defect formation in an insulating material layer deposited on an electrically conductive layer on a wafer surface according to claim 1, wherein said electrically conductive layer is a metal layer.

8. A method for determining a cause for defect formation in an insulating material layer deposited on an electrically conductive layer on a wafer surface according to claim 1, wherein said third insulating layer is an inter-metal dielectric layer.

9. A method for determining a cause for defect formation in an insulating material layer deposited on an electrically conductive layer on a wafer surface according to claim 1, wherein said first and third insulating layers are inter-metal dielectric layers.

10. A method for determining a cause for defect formation in an insulating material layer deposited on an electrically conductive layer on a wafer surface according to claim 1 further comprising the step of scanning a water jet having a pressure of preferably at least 50 kg/cm$^2$.

11. A method for determining a cause for defect formation in an insulating insulating layer deposited on an electrically conductive layer on a wafer surface according to claim 1 further comprising the step of scanning said water jet across a top surface of said third insulating layer in a path through a center of said semi-conducting wafer.

12. A method for testing a wafer having a metal conductive layer and an inter-metal dielectric (IMD) layer deposited on top comprising the steps of:

providing a silicon wafer having a first insulating layer deposited on top, depositing a second insulating layer in place of a metal conductive layer overlying said first insulating layer, depositing a third IMD layer overlying said second insulating layer, injecting a water jet of at least 50 kg/cm$^2$ pressure along a predetermined path on said third IMD layer, observing any defects formed on said third IMD layer along said predetermined path, determining a cause for defects as by water jet pressure when defects are found, and determining a cause for similar defects found previously as electrostatic discharges when no defect are found.

13. A method for testing a wafer having a metal conductive layer and an inter-metal dielectric (IMD) layer deposited on top according to claim 12, wherein said first insulating and third IMD layers are formed of silicon oxide.

14. A method for testing a wafer having a metal conductive layer and an inter-metal dielectric (IMD) layer deposited on top according to claim 12, wherein said second insulating layer deposited is silicon nitride.

15. A method for testing a wafer having a metal conductive layer and an inter-metal dielectric (IMD) layer deposited on top according to claim 12, wherein said metal conductive layer is formed of aluminum or copper.

16. A method for testing a wafer having a metal conductive layer and an inter-metal dielectric (IMD) layer deposited on top according to claim 12, wherein said first insulating and third IMD layers are formed of a material different than that used in forming said second insulating layer.

17. A method for testing a wafer having a metal conductive layer and an inter-metal dielectric (IMD) layer deposited on top according to claim 12 further comprising the step of scanning said water jet having a pressure of preferably at least 50 kg/cm$^2$.

18. A method for testing a wafer having a metal conductive layer and an inter-metal dielectric (IMD) layer deposited on top according to claim 12 further comprising the step of scanning said water jet across a top surface of said third IMD layer in a path through a center of said semi-conducting wafer.

* * * * *